US006479716B2

(12) United States Patent
Hilaly et al.

(10) Patent No.: US 6,479,716 B2
(45) Date of Patent: Nov. 12, 2002

(54) METHOD OF RECOVERING 1,3-PROPANEDIOL FROM FERMENTATION BROTH

(75) Inventors: Ahmad K. Hilaly, Springfield, IL (US); Thomas P. Binder, Decatur, IL (US)

(73) Assignee: Archer-Daniels-Midland Company, Decatur, IL (US)

( * ) Notice: Subject to any disclaimer, the term of this patent is extended or adjusted under 35 U.S.C. 154(b) by 0 days.

(21) Appl. No.: 09/808,121

(22) Filed: Mar. 15, 2001

(65) Prior Publication Data

US 2002/0133049 A1 Sep. 19, 2002

Related U.S. Application Data

(60) Provisional application No. 60/266,473, filed on Feb. 6, 2001, and provisional application No. 60/192,891, filed on Mar. 29, 2000.

(51) Int. Cl.$^7$ .......................... C07C 29/74; C07C 27/26; C07C 31/18
(52) U.S. Cl. ........................................ 568/872; 568/868
(58) Field of Search ................................ 568/872, 868, 568/869, 870; 435/158, 157, 159, 160, 161

(56) References Cited

U.S. PATENT DOCUMENTS

| | | | |
|---|---|---|---|
| 3,864,406 A | * 2/1975 | Melaja et al. | 260/637 R |
| 4,962,027 A | 10/1990 | Slininger et al. | 435/147 |
| 5,008,473 A | 4/1991 | Breitkopf et al. | 568/868 |
| 5,015,789 A | 5/1991 | Arntz et al. | 568/862 |
| 5,164,309 A | 11/1992 | Gottschalk et al. | 435/158 |
| 5,254,467 A | 10/1993 | Kretschmann et al. | 435/158 |
| 5,356,812 A | 10/1994 | Matsuyama et al. | 435/280 |
| 5,652,348 A | * 7/1997 | Burton et al. | 536/20 |
| 5,689,016 A | 11/1997 | Weider et al. | 568/862 |
| 5,723,389 A | 3/1998 | Slaugh et al. | 468/862 |
| 5,731,478 A | 3/1998 | Slaugh et al. | 568/862 |
| 5,821,092 A | 10/1998 | Nagarajan et al. | 435/158 |
| 5,841,003 A | 11/1998 | Slaugh et al. | 568/867 |
| 5,985,589 A | 11/1999 | Chantry et al. | 435/15 |

OTHER PUBLICATIONS

Barker, P.E., and Deeble, R.E., "Sequential Chromatographic Equipment for the Separation of a Wide Range of Organic Mixtures," *Chromatographia* 8:67–69, Pergamon Press (1975).

D'Aquuino, R.L., "Three Routes Vie for the 1,3-Propanediol Market," *Chemical Engineering* 106 (5):56–62, McGraw–Hill Company (1999).

Morgart, J.R., and Graaskamp, J.M., "Continuous Process Scale Chromatography," *Pittsburgh Conference on Analytical Chemistry and Applied Spectroscopy*, Paper No. 230, New Orleans, LA (Feb. 22, 1988).

* cited by examiner

*Primary Examiner*—Johann Richter
*Assistant Examiner*—Elvis O. Price
(74) *Attorney, Agent, or Firm*—Sterne, Kessler, Goldstein, Fox PLLC

(57) ABSTRACT

A method of recovering 1,3-propanediol (PDO) from fermentation broth is disclosed. The method employs ion exclusion resins to separate PDO from other impurities. The product fraction contains greater than 80% pure PDO with high yield.

14 Claims, 4 Drawing Sheets

METHOD OF RECOVERING 1,3-PROPANEDIOL FROM FERMENTATION BROTH

CROSS-REFERENCE TO RELATED APPLICATIONS

This non-provisional application is related to provisional applications No. 60/266,473, filed Feb. 6, 2001 and 60/192,891, filed Mar. 29, 2000, the content of which is incorporated herein by reference.

BACKGROUND OF THE INVENTION

Field of the Invention

The present invention relates to a method of recovering 1,3-propanediol PDO) from fermentation broth.

1. Background Art 1,3-propanediol (PDO) is a precursor of polytrimethylene terephthalate which is a raw material for making polymeric fiber. Conventionally, ethylene oxide is used to chemically produce PDO (Chopey, N., *Chemical Engineering* 106(5):56–62 (1999)). Ethylene oxide is first converted to 3-hydroxyl-opionaldehyde (3HPA) in presence of a cobalt-based catalyst. Then 3HPA is catalytically hydrogenated to produce PDO. Distillation is used to separate PDO from impurities.

Other chemical routes to 1,3-propanediol are known. For example, 1,3-propanediol can also be prepared by the catalytic solution phase hydration of acrolein followed by reduction; or from hydrocarbons such as glycerol, reacted in the presence of carbon monoxide and hydrogen over periodic table group VIII catalysts. Although it is possible to generate 1,3-propanediol by these chemical methods, they are expensive and generate waste streams containing environmental pollutants. See, for example, U.S. Pat. Nos. 5,015,789; 5,689,016; 5,723,389; 5,731,478; 5,821,092 and 5,841,003.

PDO can also be produced biochemically by fermentation (Chopey, N., *Chemical Engineering* 106(5):56–62 (1999)). In these methods, substrates such as glycerol and glucose, for example, are converted to PDO by microorganisms. See, for example, U.S. Pat. Nos. 4,962,027; 5,164,309; 5,254,467 and 5,821,092. The advantage of the fermentative route is lower raw material cost. Accordingly, there is considerable interest in making PDO fermentatively.

Methods for the purification of 1,3-propanediol are known in the art. These methods, however, use extraction with an organic solvent and distillation. See U.S. Pat. Nos. 5,254,467 and 5,356,812. A particularly good organic solvent for this process is cyclohexane (U.S. Pat. No. 5,008,473). Distillation is usually an energy intensive step. Solvent extraction uses organic solvents which can cause environmental problems. Therefore, there is a need for an effective separation method to recover PDO from fermentation broth.

Simulated moving bed (SMB) technology is a convenient and efficient method of chromatographic separation of fermentation broth (U.S. Pat. No. 2,985,589).

BRIEF SUMMARY OF THE INVENTION

It is an object of the invention to provide a method of recovering 1,3-propanediol from a liquid composition comprising a) contacting said liquid composition comprising said 1,3-propanediol with a cationic resin; b) adding solvent and eluting fractions from said resin; and c) recovering said 1,3-propanediol from a product fraction comprised of fractions of part b) comprising detectable ,3-propanediol; wherein said method of recovering lacks a distillation step.

It is a further object of the present invention to utilize simulated moving bed technology to effect the recovery of 1,3-propanediol from a liquid composition. Further object and advantages of the present invention will be clear from the description that follows.

BRIEF DESCRIPTION OF THE DRAWINGS/FIGURES

DETAILED DESCRIPTION OF THE INVENTION

It is an object of the invention to provide a method of recovering 1,3-propanediol from a liquid composition comprising a) contacting said liquid composition comprising said 1,3-propanediol with a cationic resin; b) adding solvent and eluting fractions from said resin; and c) recovering said 1,3-propanediol from a product fraction comprised of fractions of part b) comprising detectable 1,3-propanediol, wherein said method of recovering lacks a distillation step. It is a further object of the present invention to utilize simulated moving bed technology to effect the recovery of 1,3-propanediol from a liquid composition.

In one embodiment, the cationic resin is a polystyrene sulfonate strong cation exchange resin. Examples of polystyrene sulfonate strong cation exchange resins include, but are not limited to UBK555 (Mitsubishi Chemical Co., Carmel Indiana), CS11GC350 or CS11GC480 (Finex Ltd., Finland).

In a further embodiment, the size of the cationic resin is 100–500 microns. The size of the cationic resin is preferably between about 200–350 microns. In one embodiment, water is added to a 100 ml column at a flow rate of between about 0.5 to 10 ml/min, preferably about 2.6 ml/min to elute the feed material. In a further embodiment, the elution fraction were collected in volumes of about 5 ml to 200 ml, preferably about 35 ml or 140 ml.

Figure 4:
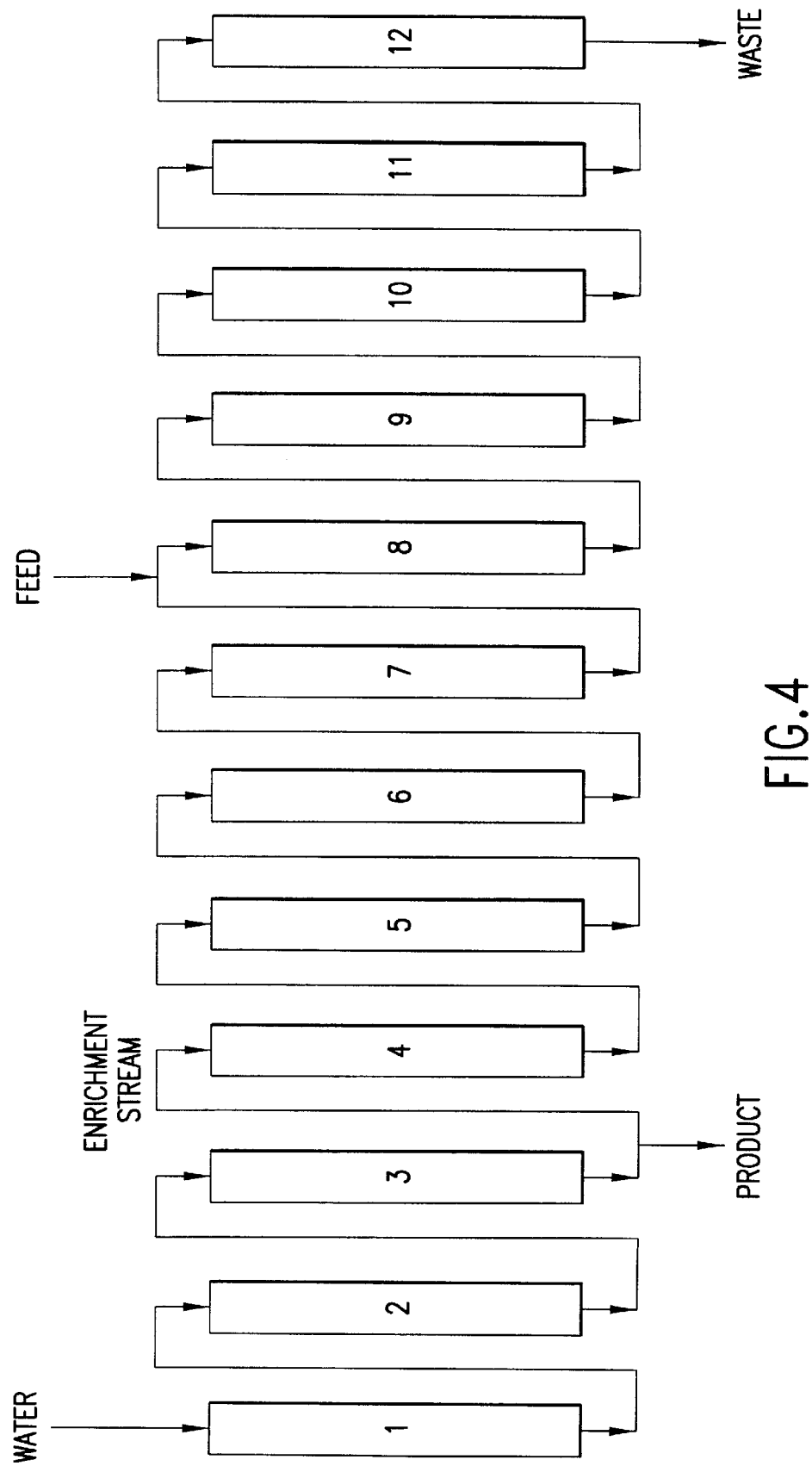
FIG. 4 shows a representative simulated moving bed apparatus used for 1,3-propanediol recovery.

In another embodiment, the method of the current invention utilizes a simulated moving bed (SMB) apparatus. SMB apparatus comprise multiple columns containing ion exchange resins are connected in series as shown in FIG. 4. SMB techniques utilize any acceptable variation of SMB apparatuses in order to accomplish significant separation of components of a feed solution. Preferably, the locations of entry ports for feed and eluent, as well as the exit ports for product and waste, are changed periodically in the direction of the fluid flow in order to simulate counter current movement of resins with respect to the fluids. Preferably, a portion of the product stream is recycled (known as enrichment stream) back to the apparatus at the port next to the product exit port. The ports divide the apparatus into multiple zones. Preferably, the apparatus consists of three zones, namely, the adsorption zone, the enrichment zone, and the elution zone. The adsorption zone includes the columns between feed entry port and waste exit port. The elution zone consists of columns between eluent entry port and product exit port. The columns between the enrichment entry port and feed entry port constitute the enrichment zone. A 4-th zone, known as reload zone, is often used in order to minimize the solvent usage. There are a few types of SMB apparatus commercially available. These apparatus can be divided into two categories, namely, moving port system and moving column system (Barker, P. E. and Deeble, R. E., *Chromatographia* 8:67–69 (1975)). The SORBEX system developed by UOP (Universal Oil Products Inc.) is an example of moving port system. Examples of moving column systems are the ADSEP system (Morgart, J. R. and Graaskamp, J. M., "Continuous Process Scale Chromatography," *Pittsburgh Conference on Analytical Chemistry and Applied Spectroscopy, Paper No.* 230, New Orleans, La. (Feb. 22, 1988)) developed by Illinois Water Treatment (IWT), and the ISEP system (Rossiter, G. J., "ISEP, A Moving Bed Contractor for Chromatographic Separations," *Fourth Workshop on Preparative HPLC*, Salzburg, Austria (Mar. 28, 1993)) developed by Advanced Separation Technologies, Inc. (AST).

In one embodiment, step-time of the SMB method can be between about 2 to 20 minutes, preferably between about 5 and 15 minutes, most preferably about 9 minutes. The resin flow rates can be from about 10 to 50 ml/min, preferably about 33.3 ml/min for a 300 ml column. In another embodiment, the flow rates of eluent, product, waste and feed streams can be between about 5 and 50 ml/min, preferably about 32.5 ml/min, about 17.3 ml/min, about 22.5 ml/min, and about 7.3 ml/min, respectively, for a 300 ml column.

It is another object of the invention to provide a method for recovering 1,3-propanediol from a liquid composition wherein said liquid composition comprises fermentation broth or compositions which mimic fermentation broth. In one embodiment, the liquid composition comprises about 1–50% 1,3-propanediol. In another embodiment, the liquid composition comprises about 5–24% 1,3-propanediol. In a preferred embodiment of the method, the solvent is water.

In one embodiment of the method of claim 1, the product fraction of part c) comprises at least 50% 1,3-propanediol. In another embodiment, the product fraction of part c) comprises at least 75% 1,3-propanediol. In a preferred embodiment of the method, the product fraction of part c) comprises at least 85% 1,3-propanediol.

It is another object of the invention to provide a method for identifying eluted fractions lacking detectable 1,3-propanediol and recycling the fractions back to the fermentation process.

The term "fermentation" as used herein is intended to comprise the processes of bioconversion and bioproduction of PDO. Further, the term comprises one or more of the processes, occurring alone, sequentially or together, and at any growth stage (stationary, plateau, replicating, etc.) of the microorganism.

In the present invention, it is an object to provide a method for recovery of PDO. Biological microorganisms producing PDO by bioconversion and/or bioproduction are cultured by methods known in the art. The microorganisms are grown aerobically or anaerobically in a suitable liquid composition, for example, fermentation broth, which contains sources of carbon, nitrogen, and inorganic salts assimilable by the microorganism.

The liquid compositions can be any fermentation broth, any nutrient medium or any culture medium. Any liquid composition suitable for bioproduction of, and/or bioconversion to, PDO is envisioned in the practice of the invention. Any liquid composition comprising one or more carbon sources which a microorganism can utilize may be employed.

As used herein, a "carbon source" means any carbon source capable of being metabolized by a microorganism where the source contains at least one carbon atom. As the sources of carbon, there can be employed various carbohydrates such as glucose, fructose, sucrose, dextrin, starch, etc., alcohols such as sorbitol, ethanol, glycerol, etc., organic acids such as fumaric acid, citric acid, acetic acid, propionic acid, etc. and the corresponding salts, hydrocarbons such as paraffin, and various mixtures thereof. Other sources which can be utilized include triglycerides from any plant or animal sources, treated and untreated triglyceride processing streams and glycerol water from methanolysis of fats or oils, or soap splitting. See, for example, U.S. Pat. Nos. 5,164,309; 5,253,467 and 5,356,812.

Many inorganic, organic and proteinaceous materials can be used as nitrogen sources in the liquid composition in the bioconversion/bioproduction process. The inorganic sources of nitrogen include, among others, inorganic acid ammonium salts such as ammonium chloride, ammonium sulfate, ammonium phosphate, etc. Organic acid ammonium salts such as ammonium fumarate, ammonium citrate etc. can also be used. Other suitable nitrogen sources include, for example, sources of nitrate or ammonium ions, urea, yeast extract, beef extract, proteose peptone, soybean meal, hydrolysates of casein, distiller's solubles, and the like. The distiller's solubles can be corn steep liquor, bottom stillage from ethanol distillation or soybean solubles. Among the inorganic salts that can be incorporated into the nutrient medium are the customary salts capable of yielding calcium, zinc, iron, manganese, magnesium, copper, cobalt, phosphorous, sulfate, chloride, borate, molybdenum and like ions. Where necessary, there can also be incorporated factors which promote growth of the strain used, such as vitamins. See, for example, U.S. Pat. Nos. 4,962,027; 5,254,467 and 5,356,812.

After fermentation, which can be batch fermentation or continuous fermentation, the broth is separated from the microorganisms. Separation of the microorganisms from the broth is by any method known to those in the art. Separation of the microorganisms from the broth results in a material suitable for ion exchange chromatography. Impurities in fermentation broth typically include unconverted sugars, residual salts and by-products. The proposed separation method utilizes ion-exclusion chromatography to reject salts, sugars and other materials. In this method, ionic components are rejected due to ionic repulsion. The non-ionic components enter the pores of the stationary phase and, therefore, elute from a column later than the ionic components. The chemical nature of PDO is non-ionic. Therefore, PDO elutes from column later than other ionic components (e.g. salts). The fermentation by-products and sugars elute earlier than PDO because of differences in molecular properties. In this invention, two fractions from a column are collected. The first fraction contains impurities and contains mainly salts; sugars and other by-products. The first fraction can be recycled back to fermentation for further utilization of residual carbon sources and other ingredients. The second fraction contains mainly PDO with high purity values. By varying the number of effluent fractions which are combined and which form a product fraction, the purity of PDO in the product fraction can be varied from at least 50% to greater than 90%, preferably 99%, more preferably about 100%.

EXAMPLES

Example 1

Figure 1:
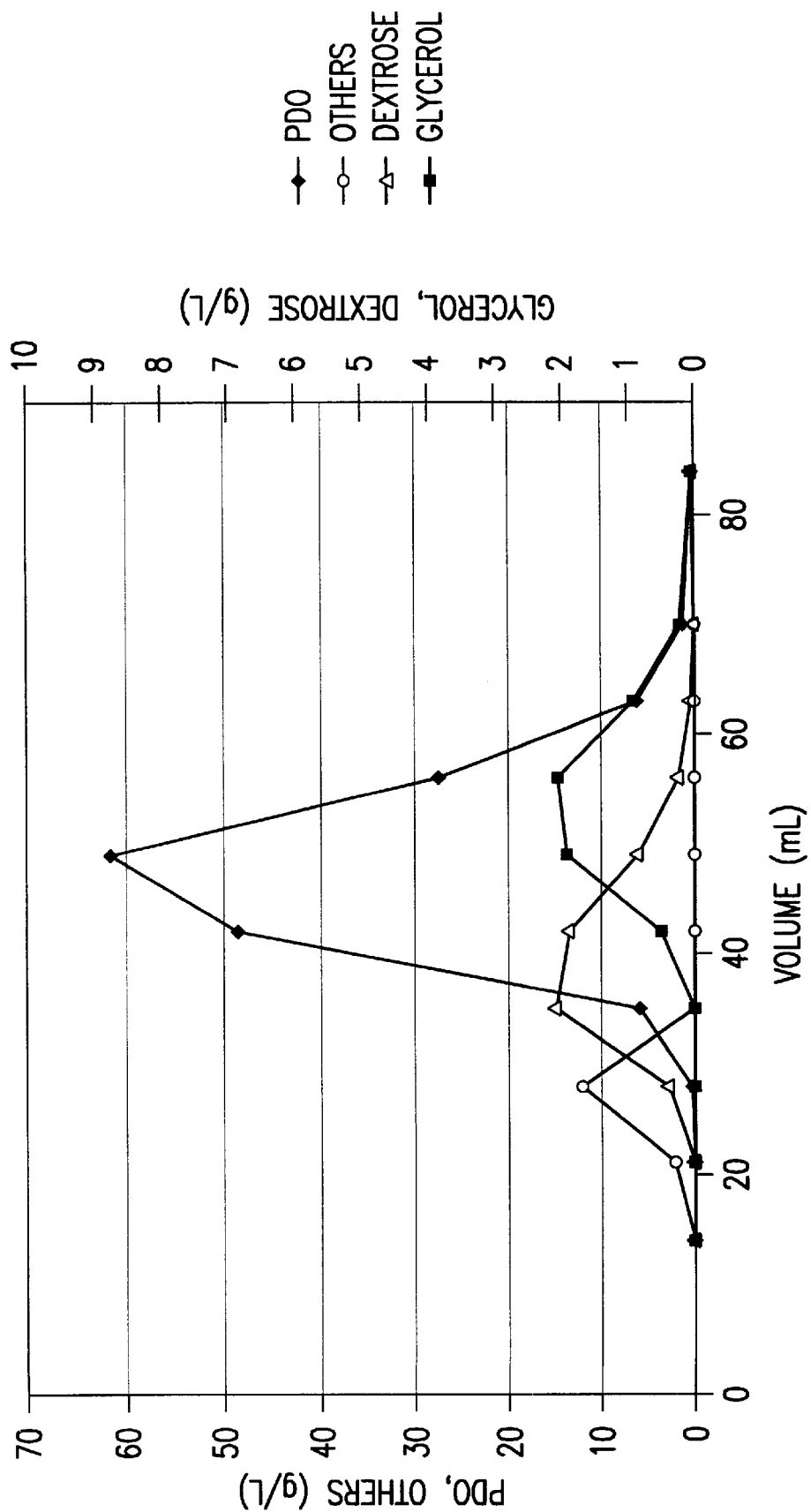
FIG. 1 shows the results of a pulse test with the resin UBK555 in Na-form. The term "others" indicate components consisting mainly of various salts.

A pulse test was carried out in a column containing 100 ml of a cation exchange resin (UBK555)(Mitsubishi Chemical Corporation) in the Na-form. The UBK555 resin is a polystyrene sulfonate strong acid cation resin with a narrow particle size distribution (200–240 microns). A feed material was formulated in the laboratory by mixing 1,3-propane diol (PDO) and corn steep liquor in order to mimic the fermentation broth. The concentration of PDO in the feed was 56.6 g/L. About 10 ml of the feed material was added to the top of the column. Water was added to the column at a flow rate of 2.6 ml/min to elute the feed material. FIG. 1 shows the effluent profile. The product fraction consisting of the effluent from 35 ml to 140 ml (a net volume of 105 ml) was 87% pure. The recovery of PDO in the product fraction was 95.7%.

Example 2

Figure 2:
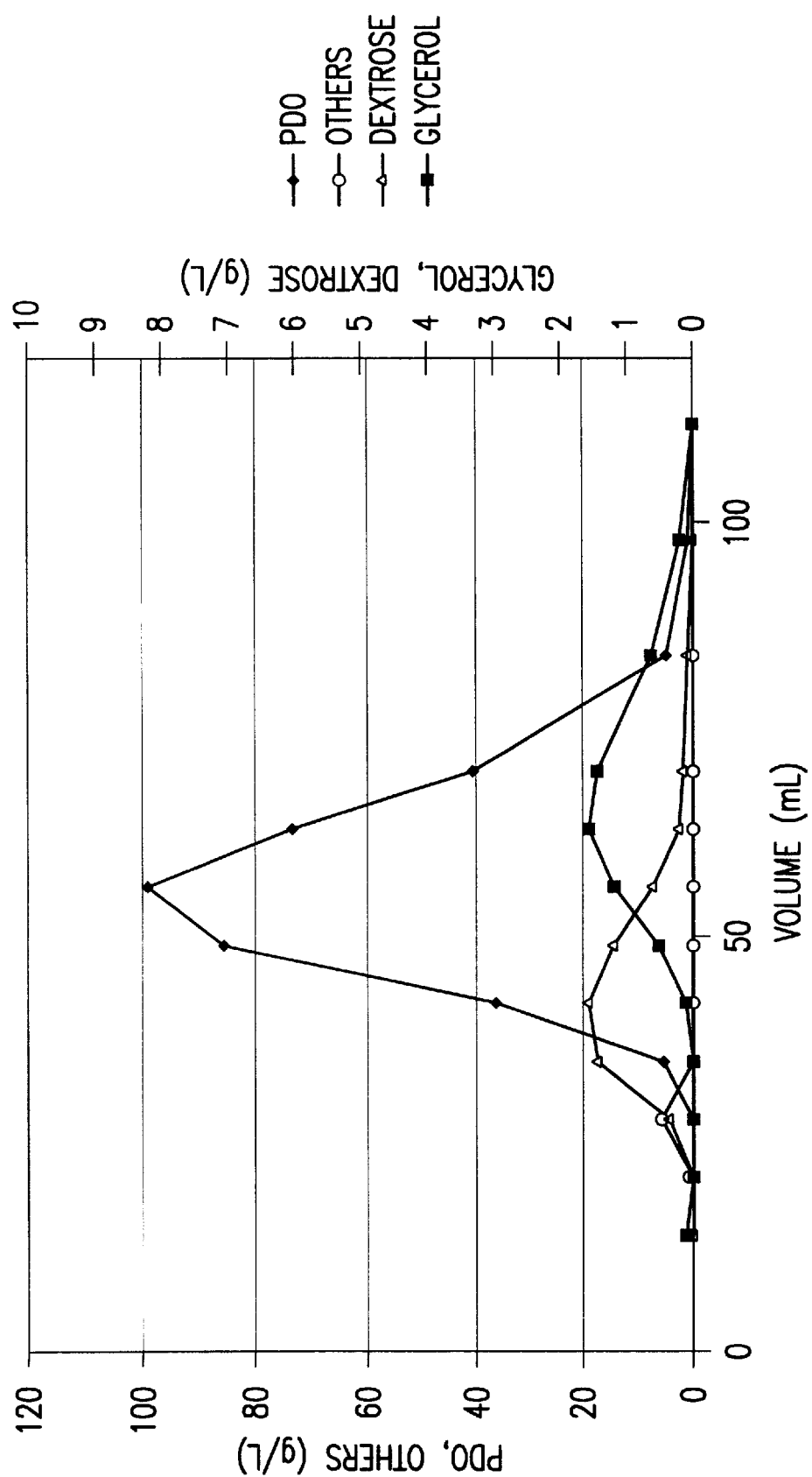
FIG. 2 shows the results of a pulse test with the resin UBK555 in Ca-form.

A pulse test was carried out in a column containing 100 ml of a cation exchange resin (UBK555) in the Ca-form. A feed material was formulated in the laboratory by mixing 1,3-propanediol (PDO) and bottom stillage from an ethanol distillation column in order to mimic the fermentation broth. The concentration of PDO in the feed was 239.9 g/L. About 10 ml of the feed material was added to the top of the column. Water was added to the column at a flow rate of 2.6 ml/min to elute the feed material. FIG. 2 shows the effluent profile. The product fraction consisting of the effluent from 35 ml to 140 ml (a net volume of 105 ml) was 92.4% pure. The recovery of PDO in the product fraction was 98.4%.

Example 3

Figure 3:
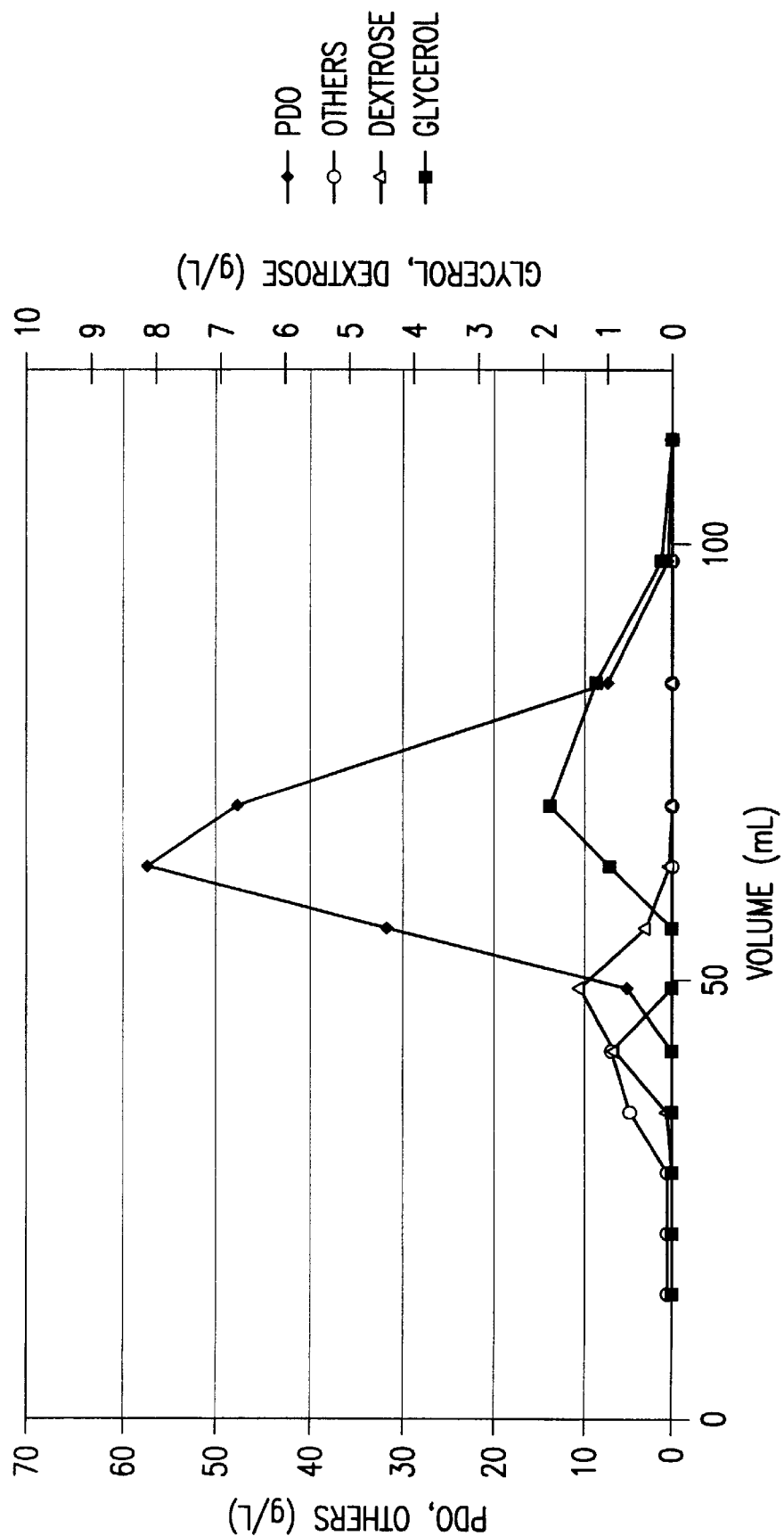
FIG. 3 shows the results of a pulse test with the resin CSI IGC350 in Ca-form.

A pulse test was carried out in a column containing 100 ml of a cation exchange resin (CS11GC350) in the Ca-form. The CS11GC 350 resin is a apolystyrene sulfonate strong cation exchange resin with a mean particle size of 350 microns. A feed material was formulated in the laboratory by mixing 1,3-propanediol (PDO) and bottom stillage from an ethanol distillation column in order to mimic the fermentation broth. The concentration of PDO in the feed was 239.9 g/L. About 10 ml of the feed material was added to the top of the column. Water was added to the column at a flow rate of 2.6 ml/min to elute the feed material. FIG. 3 shows the effluent profile. The product fraction consisting of the effluent from 49 ml to 140 ml (a net volume of 91 ml) was 88.1% pure. The recovery of PDO in the product fraction was 96.7%.

Example 4

Simulated Moving Bed (SMB) experiments were carried out wherein 12 columns were loaded with 300 ml of a cationic resin (CS11 GC480) in a Ca-form. The columns were arranged in series suing the configuration as shown in FIG. 4. In this setup, the columns mover intermittently in an opposite direction relative to the direction of the fluid. Water was used as the eluent. A feed material was formulated in the laboratory by mixing 1,3-propanediol (PDO), dextrose and bottom stillage from an ethanol distillation column in order to mimic fermentation broth. A step-time of 9 minutes was used for all the experiments. This was equivalent to 33.3 ml/min of resin flow rate. The flow rates of eluent, product, waste and feed streams were 32.5 ml/min, 17.3 ml/min, 22.5 ml/min, and 7.3 ml/min respectively. The operations were carried out at ambient temperature. The experiments resulted in a product with 89.4% purity. The yield was 99.5%.

Having now fully described the present invention in some detail by way of illustration and example for purposes of clarity of understanding, it will be obvious to one of ordinary skill in the art that same can be performed by modifying or changing the invention with a wide and equivalent range of conditions, formulations and other parameters thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent if each individual publication, patent or patent application was specifically and individually indicated to be incorporated by reference.

What is claimed is:

1. A method of recovering 1,3-propanediol from fermentation broth comprising:
    (a) contacting said fermentation broth comprising said 1,3-propanediol with a cationic resin using ion exclusion chromatography;
    (b) adding solvent and eluting fractions from said resin; and
    (c) recovering said 1,3 propanediol from a product fraction comprised of fractions of part b) comprising detectable 1,3-propanediol; wherein said method of recovering lacks a distillation step.

2. The method of claim 1 wherein said cationic resin is a polystyrene sulfonate strong cation exchange resin.

3. The method of claim 1 wherein said method of recovery of 1,3-propanediol is conducted using a simulated moving bed apparatus.

4. The method of claim 1 wherein said method of recovery of 1,3-propanediol is conducted using a simulated moving bed technique.

5. The method of claim 1 wherein the size of the cationic resin is 100–500 microns.

6. The method of claim 4 wherein the size of the cationic resin is 200–350 microns.

7. The method of claim 1 wherein said liquid composition comprises fermentation broth or compositions which mimic fermentation broth.

8. The method of claim 6 wherein said liquid composition comprises 1–50% 1,3-propanediol.

9. The method of claim 7 wherein said liquid composition comprises 5–24% 1,3-propanediol.

10. The method of claim 1 wherein said solvent is water.

11. The method of claim 1 wherein said product fraction of part c) comprises at least 50% 1,3-propanediol.

12. The method of claim 1 wherein said product fraction of part c) comprises at least 75% 1,3-propanediol.

13. The method of claim 1 wherein said product fraction of part c) comprises at least 85% 1,3-propanediol.

14. The method of claim 1, wherein said eluted fractions lacking detectable 1,3-propanediol are identified and recycled back into the fermentation process.

* * * * *